United States Patent [19]

Segall et al.

[11] Patent Number: 4,920,137

[45] Date of Patent: Apr. 24, 1990

[54] METHOD FOR STABILIZING ISOTHIAZOLINONES

[75] Inventors: Jeane Segall; Leonard M. Shorr, both of Haifa, Israel

[73] Assignee: Bromine Compounds Limited, Israel

[21] Appl. No.: 222,130

[22] Filed: Jul. 21, 1988

[30] Foreign Application Priority Data

Jul. 23, 1987 [IL] Israel .......................................... 83305
Jul. 15, 1988 [IL] Israel .......................................... 87111

[51] Int. Cl.$^5$ .................... A61K 31/425; C07D 275/02
[52] U.S. Cl. ...................................... 514/372; 548/213
[58] Field of Search ......................... 548/213; 514/372

[56] References Cited

U.S. PATENT DOCUMENTS

| 3,870,795 | 3/1975 | Miller et al. .......................... 514/372 |
| 4,067,878 | 1/1978 | Miller et al. .................. 548/101 XR |
| 4,105,431 | 8/1978 | Lewis et al. ............................... 71/67 |
| 4,318,835 | 3/1982 | Clarke .................................... 264/36 |
| 4,724,201 | 2/1988 | Okazaki et al. .............. 548/157 XR |

FOREIGN PATENT DOCUMENTS 0106563 4/1984 European Pat. Off. .
0166611 1/1986 European Pat. Off. .
0194146 9/1986 European Pat. Off. ............ 514/372

OTHER PUBLICATIONS

"The Condensed Chemical Dictionary", 6th ed., Reinhold Publishing Corporation, New York, (1961), pp. 184, 590.

Primary Examiner—Diana G. Rivers
Attorney, Agent, or Firm—Lerner, David, Littenberg, Krumholz & Mentlik

[57] ABSTRACT

A method for stabilizing compositions containing one or more 3-isothiazolinones, which method includes adding to the 3-isothiazolinone composition an amount effective to stabilize the composition of one or more stabilizing compounds having the formula:

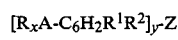

wherein Z is selected from $AR_x$, $R^1$, $R^2$, alkoxymethylene, methylene and alkylidene; R, $R^1$ and $R^2$ are independently selected from hydrogen, straight-chained, branched and cyclic alkyl, aryl and arylalkyl; A is oxygen or nitrogen, provided that when A is oxygen, x is 0 or 1, when A is nitrogen, x is 1 or 2; and y is 1 or 2.

22 Claims, No Drawings

METHOD FOR STABILIZING ISOTHIAZOLINONES

The present invention relates to a method for stabilizing isothiazolinones. More particularly, the present invention relates to a method for stabilizing 3-isothiazolinones of the formula (1):

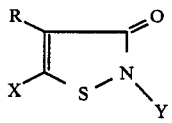  (1)

wherein X represents hydrogen or a halogen, Y is an alkyl, alkenyl, cycloalkyl, aralkyl or aryl group and R is hydrogen, halogen or an alkyl radical.

Such compounds are known to possess biocidal and biostatic activity towards a variety of organisms. The isothiazolinones of this type, however, are often not obtained in free form, but as complexes of the formula (2):

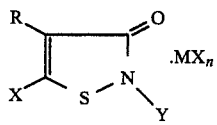  (2)

wherein M is a cation or an amine, X is an anion forming a compound with the cation M, and the value of n is such that the anion $X_n$ satisfies the valence of M. The complexes of formula (2), described in U.S. Pat. No. 4,067,878, are said to be more stable than the 3-isothiazolones of formula (1).

The term alkyl group for the substituents R and Y is intended to include both unsubstituted or substituted alkyl, alkenyl, cycloalkyl, aralkyl or aryl groups. In a preferred embodiment the alkyl group is selected from methyl and n-octyl.

Examples of the cation M are metal cations such as calcium, copper, magnesium, manganese, nickel and zinc and complexes of the metal ions such as complexes with ammonia and amines.

For bactericidal and fungicidal purposes, particularly useful compositions, described in U.S. Pat. No. 4,105,431, comprise a mixture of N-alkyl-isothiazolin-3-one and N-alkyl-5-chloro-isothiazolin-3-one, in a weight ratio of about 1:3 respectively. A particularly useful mixture of this kind is that in which Y is a methyl group, and such a mixture is referred to hereinafter as MIT (methylisothiazolinones).

Formulations of MIT in water or in solvent media containing hydroxylic groups are unstable, decompose rapidly and cannot be stored for long periods of time. The art has searched for ways to overcome this stability problem for a long time. A solution suggested in the art comprises stabilizing 3-isothiazolinones either in liquid formulations or on solid supports, by the addition of metal nitrates. Some such methods are described, e.g., in U.S. Pat. No. 3,870,795, U.S. Pat. No. 4,067,878, EP 0 106 563 and EP 0 166 611. Such methods have the considerable drawback of requiring the addition of metal nitrates in amounts which are usually nearly equimolar—but often even in excess—with respect to the 3-isothiazolinones. Furthermore, the addition of nitrates may lead to the presence of nitrosamines, which are highly undesirable impurities which are suspected of being carcinogens. Therefore, the methods of the art have the added disadvantage of requiring means for removing such nitrosamines or their precursors, as disclosed, e.g., in EP 0 095 907, or for inhibiting their formation. Such operations are complicated, time-consuming and do not afford the certainty that a sufficient amount of nitrosamines or of their precursors has been removed.

It is therefore clear that it would be very desirable to provide a method for stabilizing solutions of 3-isothiazolinones, without the need of employing materials which react to give nitrosamines, or at least to reduce the amount of nitrosamines in the formulation to a very low level. Furthermore, certain systems, e.g., petroleum, cannot be treated with the formulations stabilized according to the art, since they cannot be contaminated with large amounts of magnesium nitrate.

It has now surprisingly been found, and this is an object of the invention, that it is possible to provide a method by which 3-isothiazolinones and mixtures of two or more 3-isothiazolinones can be stabilized in solid form, in an aqueous medium, or in an organic medium comprising hydroxylic groups, without the need to employ large amounts of metal nitrates as stabilizers.

It is a further object of the invention to provide stable 3-isothiazolinones mixtures of the kind described above, which are substantially free of nitrosamines and of nitrosamine producers.

It has further been found, and this is still another object of the invention, that aerating stabilized MIT compositions has a beneficial effect on the final stability of the composition.

While it has been known to package and transport MIT solutions according to the known art in containers which are incompletely filled, because of ease and safety in handling and discharge operations, the art has not specifically addressed the question of the influence of aeration to the stability of MIT. Indeed, although the mechanism by which aeration aids stabilization of compositions according to the invention has not been fully elucidated, aeration would not seem to influence the stability of MIT solutions stabilized according to the known art. By "aeration" is meant the exposure of the stabilized MIT solution to air or to another comparable gaseous medium.

The method for stabilizing 3-isothiazolinones of the formula (1), according to the invention, is characterized in that a stabilizing effective amount of a stabilizing compound of the formula (3):

$$[R_xA\text{-}C_6H_2R^1R^2]_y\text{-}Z$$

wherein:
R, $R^1$ and $R^2$ each independently represents hydrogen, a straight-chained or branched or cyclic alkyl radical, aralkyl or aryl;
A is oxygen or nitrogen;
Z represents $AR_x$, $R^1$, $R^2$, alkoxy methylene, methylene or alkylidene;
provided that when A is oxygen, x is 0 or 1 and when A is nitrogen, x is 1 or 2; and y is 1 or 2; is added to the composition containing a 3-isothiazolinone or two or more 3-isothiazolinones.

A preferred group of stabilizers, which possesse enhanced stabilization properties, consists essentially of hydroquinone, quinone and quinhydrone, and their derivatives and homologues. Other representative stabilizing compounds are, e.g., tert-butylcatechol, p- methoxyphenol, and p-phenylenediamine and its derivatives.

A considerable advantage of the method of the invention lies in that very low amounts of a stabilizing compound of formula (3), or of a derivative thereof, can be employed. Thus, according to one embodiment of the invention the concentration of the stabilizing compound of the invention in a 3-isothiazolinones—containing liquid composition is lower than 10%, for a solution of about 15% 3-isothiazolinones.

According to a preferred embodiment of the said invention, the composition to be stabilized comprises a mixture of N-alkyl-isothiazolin-3-one and N-alkyl-5-chloro-isothiazolin-3-one. Particularly useful mixtures of this kind are those in which the N-alkyl radical is a N-methyl radical.

The invention is also directed to stable compositions containing one or more 3-isothiazolinones and a stabilizing effective amount of a compound of the formula (3):

wherein:
R, $R^1$ and $R^2$ each independently represents hydrogen, a straight-chained or branched or cyclic alkyl radical, aralkyl or aryl;
A is oxygen or nitrogen;
Z represents $AR_x$, $R^1$, $R^2$, alkoxy methylene, methylene or alkylidene;
provided that when A is oxygen, x is 0 or 1, and when A is nitrogen, x is 1 or 2; and y is 1 or 2.

Preferred stable compositions of the invention are those which contain a mixture of N-alkyl-isothiazolin-3-one and N-alkyl-5-chloro-isothiazolin-3-one, still more preferably wherein the N-alkyl radical is a N-methyl radical.

While the presence of metal nitrate stabilizers in the compositions of the invention is not necessary, such nitrate stabilizers could be also added, together with the stabilizing compound(s) of the invention. It has been surprisingly found that adding to the composition to be stabilized also one or more metal salt(s), selected from metal nitrate stabilizers and salts of metals of groups IA and IIA of the periodic table of the elements, provides a synergistic stabilizing effect, and may be convenient in some cases. In any case, the synergistically effective amount of metal nitrate stabilizers employed in any given composition of the invention can be much lower than amounts used in the known art and hence the amount of nitrosamines or nitrosamine precursors would be drastically reduced.

By "synergistically effective amounts" is meant any amount which, while by itself incapable of effectively stabilizing 3-isothiazolinones, improves the stabilization of 3-isothiazolinone formulations which is provided by the sole addition of stabilizing effective amounts of a stabilizing compound of the invention.

Preferred metal salts are selected from the group consisting of magnesium nitrate, $K_2HPO_4$, KH phthalate, magnesium acetate and potassium permanganate.

The invention also encompasses novel stabilizing compounds for stabilizing solutions comprising one or more 3-isothiazolinones, the said novel stabilizers being compounds of the formula (3):

wherein:

R, $R^1$ and $R^2$ each independently represents hydrogen, a straight-chained or branched or cyclic alkyl radical, aralkyl or aryl;
A is oxygen or nitrogen;
Z represents $AR_x$, $R^1$, $R^2$, alkoxy methylene, methylene or alkylidene;
provided that when A is oxygen, x is 0 or 1 and when A is nitrogen, x is 1 or 2; and y is 1 or 2.

Preferred stabilizing compounds of the invention comprise hydroquinone, quinone and quinhydrone, and their derivatives and homologues.

Stable compositions comprising one or more 3-isothiazolinones, whenever prepared according to the method of the invention, also form part of the present invention. Such compositions comprise solid and liquid formulations comprising one or more 3-isothiazolinones, particularly those in which the solvent medium is essentially water, or a solvent medium containing hydroxylic groups.

The above and other characteristics and advantages of the invention will be better understood through the following illustrative and non-limitative examples thereof. The following examples represent stability tests performed at elevated temperatures, in order to accelerate decomposition. For reference purposes it should be noted that a correlation of the elevated temperature testing to ambient temperature is described in EP 0 166 611. For instance, for a formulation containing 1.5% of isothiazolinones one week at 50° C. was found to be equivalent to two months of storage at ambient temperature. The results obtained by the inventors confirm the above correlation. All percentages given in the following examples refer to weight percent.

The following examples refer to MIT as the representative formulation. MIT concentrations were determined in all cases by HPLC analysis. In the synthesis of MIT, mercaptoamides are cyclochlorinated in the presence of inert liquid media. The major part of the MIT produced generally precipitates. The product can be recovered in several ways, viz., by filtering off the precipitate and recycling the mother liquor, by evaporating the solvent leaving all the products in the residual solid, or by extracting the product into a second liquid phase, such as water, essentially insoluble in the reaction medium. While the method of the invention is valid for stabilizing MIT independent of its source, differences can be found between different samples, depending on their source. Care should therefore be exercised in comparing results, and results obtained in different examples employing different materials may be not comparable.

EXAMPLE 1

A comparative test was run to determine the influence of hydroquinone as a stabilizer, at a concentration of 0.2 wt%. The formulation employed was an MIT aqueous solution, containing a mixture of 5-H/5-Cl isothiazolinones in a weight ratio of 1:2. The accelerated stability test was run at 50° C. Compositions containing hydroquinone were tested during 30 days, while for compositions free of hydroquinone the test was discontinued after 8 days, due to the very high level of decomposition attained (67%). The results of these tests are shown in Table I and are self-explanatory.

EXAMPLE 2

A series of tests was run with a MIT formulation containing 11.5% MIT in water, to determine the influence of different levels of hydroquinone on the stability of the formulation. The tests were run at 50° C. as in Example 1. The results of these tests are shown in Table II. As seen from the data in the table, hydroquinone levels as low as 0.5% were sufficient to insure total stability for at least 40 days, and after 50 days only 5% decomposition occurred. Increasing the amount of hydroquinone from 1% to 4%, on the other hand, increased the stability of the MIT formulation fourfold in terms of time.

EXAMPLE 3

An accelerated stability test was run to determine the relative efficacy of different stabilizers. The formulation tested contained 12.3 wt% MIT in water. The test was run for 8 days at 50° C.

The results reported in Table III show that the most effective stabilizer among the ones tested was p-methoxyphenol, which limited the decomposition to 5%, as compared to the 60% decomposition of the control formulation (free of stabilizer).

EXAMPLE 4

The stability of a 10.3% MIT formulation in a solvent mixture of 80:20 w/w dipropyleneglycol/water was tested at 50° C., using a 0.5% concentration of two stabilizers: hydroquinone and tert-butylcatechol. The test was run for 4 days and no appreciable difference was found between the stabilizing effects of the two stabilizers tested. The results of this test are shown in Table IV.

EXAMPLE 5

The stability of a 5.7% formulation of MIT in dipropylene glycol was tested at 50° C. using N,N'-di-sec-butyl-p-phenylene-diamine as the stabilizer. The formulation so stabilized was tested after 5 days versus an identical control formulation which contained no stabilizer. The decomposition of the stabilized formulation was 17%, while that of the control formulation was 99%.

EXAMPLE 6

Example 5 was repeated, using 2-n-octyl-3-isothiazolinone instead of MIT. After 5 days, only 25% of the stabilized isothiazolinone decomposed, while the control formulaton was essentially completely decomposed.

EXAMPLE 7

This example illustrates the synergistic effect of metal nitrates, together with the stabilizing compounds of the invention. An accelerated stability test was carried out as in the previous examples at 50° C., to test the stability of a 10.8 wt% solution of MIT (crude) in water. Four different formulations were tested, containing magnesium nitrate hexahydrate and hydroquinone, both alone and in admixture thereof, as well as a control formulation containing no stabilizers. The results of these tests are reported in Table V. The results of these tests clearly show that hydroquinone was a far better stabilizer than magnesium nitrate at the level used, and their combination provided even better results.

EXAMPLE 8

A mixture of MIT and 4,5-dichloro-2-methyl-isothiazolone (90/10 w/w-total concentration 11.0%) was stabilized using a mixture of 1 wt% $Mg(NO_3)_2 \cdot 6H_2O$ and 1 wt% Hydroquinone. The results obtained were comparable to those obtained in Example 7 for the same stabilizing mixture.

EXAMPLE 9

A 9.5 wt% crude MIT aqueous formulation was tested in the accelerated stability test at 50° C. The results of this test are set out in Table VI, from which the beneficial effect of hydroquinone on even large amounts of $Mg(NO_3)_2$ can be seen.

EXAMPLE 10

In order to illustrate the synergistic effect of different salts on the extent of stabilization, four different samples were prepared using the same MIT source, each containing about 10% (±8%) MIT (crude). Stability of the composition was tested without any stabilizer, with 1% hydroquinone (HQ) as a stabilizer, and with the addition of a salt to HQ. The salts employed were $K_2HPO_4$, KH phthalate, Magnesium acetate and $KMnO_4$. The results of these tests are set out in Tables VII to X, which are self-explicative as to the marked synergistic effect obtained by the addition of these salts. Accelerated stability tests were carried out at 65° C.

EXAMPLE 11

Three identical 10 ml samples of a 11.6% MIT containing 1 wt% $Mg(NO_3)_2 \cdot 6H_2O$ and each 1 wt% of a different stabilizer selected from among hydroquinone (HQ), quinhydrone (QH) and quinone (Q). Stability was tested at 50° C. A composition was considered as destabilized when more than 10% MIT decomposition occurred. The results of the comparative test are set forth in Table XI below.

EXAMPLE 12

The compositions of Runs 1 and 3 of Example 11 were tested under a nitrogen atmosphere, to determine the relative potency of quinone and hydroquinone. While different stability periods were obtained with different MIT samples, samples containing quinone were found to be stable for periods almost twice as long as those containing hydroquinone, from which it can be concluded that the synergistic effect with magnesium nitrate hexahydrate is considerably more pronounced with quinone.

EXAMPLE 13

Differently aerated MIT compositions were tested for stability at 50° C. The vessel employed was in all cases a 300 ml glass bottle, and all compositions contained 1 wt% hydroquinone, together with 1 wt% $Mg(NO_3)_2 \cdot 6H_2O$. The results of these tests are set forth in Table XII.

The above examples have been provided for the purpose of illustration, and are not intended to be limitative. Many different formulations and solvents can be employed, different concentrations of stabilizers can be employed or different 3-isothiazolinones concentrations can be used, all without exceeding the scope of the invention.

TABLE I

| Influence of hydroquinone at 0.2% concentration level | | | | | |
|---|---|---|---|---|---|
| No Additive | | | Hydroquinone Added | | |
| Time (days) | MIT Conc. wt % | % Decomposition | Time (days) | MIT Conc. wt % | % Decomposition |
| 0 | 11.6 | 0 | 0 | 11.6 | 0 |

TABLE I-continued

Influence of hydroquinone at 0.2% concentration level

| No Additive | | | Hydroquinone Added | | |
|---|---|---|---|---|---|
| Time (days) | MIT Conc. wt % | % Decomposition | Time (days) | MIT Conc. wt % | % Decomposition |
| 4 | 10.3 | 10 | 4 | 11.6 | 0 |
| 8 | 3.8 | 67 | 8 | 11.6 | 0 |
| | | | 12 | 11.6 | 0 |
| | | | 20 | 11.6 | 0 |
| | | | 30 | 8.1 | 30 |

TABLE II

Influence of Concentration Level of Hydroquinone (HQ)

| Decomposition at Time T (days): | HQ Conc. wt %: None | 0.15% | 0.2% | 0.5% | 1.0% |
|---|---|---|---|---|---|
| 5 | 15% | 0 | 0 | 0 | 0 |
| 10 | 85% | 15% | 0 | 0 | 0 |
| 15 | | 35% | 0 | 0 | 0 |
| 20 | | | 0 | 0 | 0 |
| 30 | | | 30% | 0 | 0 |
| 40 | | | | 0 | 0 |
| 50 | | | | 5% | 0 |
| 60 | | | | 32% | 0 |
| 70 | | | | | 15% |

TABLE III

Influence of Various Additives at 0.2% Concentration
Decomposition of Formulation After 8 days

| No additive | 60% |
|---|---|
| AO 23[a] | 50% |
| p-MeO-Ph[b] | 5% |
| t-Bu-Cat[c] | 15% |
| BHA[d] | 20% |

[a] N,N-diisopropyl-p-phenylenediamine
[b] p-methoxyphenol
[c] tert-butylcatechol
[d] tert-butyl-hydroxyanisole

TABLE IV

Influence of Additives at 0.5% Concentration
Decomposition after 4 days

| No additive | 70% |
|---|---|
| Hydroquinone | 1% |
| tert-Butylcatechol | 1% |

TABLE V

Synergistic Effect.

| Decomposition at Time T (days): | None | (1) Mg | (2) HQ | (3) Mg + HQ | (4) 2HQ |
|---|---|---|---|---|---|
| 6 | 60% | 46% | 0 | 0 | 0 |
| 30 | | | 0 | 0 | 0 |
| 37 | | | 47% | 0 | 18% |
| 48 | | | | 0 | 62% |
| 55 | | | | 8% | |
| 60 | | | | 27% | |

(1) Mg(NO$_3$)$_2$.6H$_2$O (1 wt %)
(2) Hydroquinone (1 wt %)
(3) 1% Mg + 1% HQ
(4) Hydroquinone (2 wt %)

TABLE VI

Synergistic Effect on 9.5% MIT Formulation

| Additive: | None | 28 Mg[1] | 28 Mg + 1 HQ[2] |
|---|---|---|---|
| Decomposition at time T: | | | |
| T = 3 days | 63% | 0 | 0 |
| T = 14 days | | 36% | 20% |
| T = 20 days | | 42% | 20% |

[1] 28% Mg(NO$_3$)$_2$.6H$_2$O
[2] 28% Mg(NO$_3$)$_2$.6H$_2$O + 1% Hydroquinone

TABLE VII

Synergistic Effect on 10% MIT formulation (65° C.)

| Additive | None | 2% K$_2$HPO$_4$ | 1% HQ | 2% K$_2$HPO$_4$ + 1% HQ |
|---|---|---|---|---|
| Decomposition at time T: | | | | |
| T = 3 days | 63% | 49% | 10% | 0 |
| T = 6 days | | | 61% | 0 |
| T = 10 days | | | | 4% |
| T = 16 days | | | | 25% |
| T = 20 days | | | | 72% |

TABLE VIII

Synergistic Effect on 10% MIT formulation (65° C.)

| Additive | None | 1% KH phthalate | 1% HQ | 1% KH phthalate + 1% HQ |
|---|---|---|---|---|
| Decomposition at time T: | | | | |
| T = 3 days | 63% | 47% | 10% | 0 |
| T = 6 days | | | 61% | 10% |
| T = 10 days | | | | 40% |

TABLE IX

Synergistic Effect on 10% MIT formulation (65° C.)

| Additive | None | 1% Mg acetate* | 1% HQ | 1% Mg acetate + 1% HQ |
|---|---|---|---|---|
| Decomposition at time T: | | | | |
| T = 3 days | 63% | 60% | 10% | 4% |
| T = 6 days | | | 61% | 14% |

*Mg(CH$_3$COO)$_2$.4H$_2$O

TABLE X

Synergistic Effect on 10% MIT formulation (65° C.)

| Additive | None | 1% KMnO$_4$ | 1% HQ | 1% KMnO$_4$ + 1% HQ |
|---|---|---|---|---|
| Decomposition at time T: | | | | |
| T = 4 days | 31% | 35% | 10% | 0 |
| T = 7 days | | | 61% | 0 |
| T = 13 days | | | | 17% |

TABLE XI

Relative Influence of HQ, QH and Q
on 11.6% MIT formulation (50° C.)

| Run No. | Additive | Stability Period (days) |
|---|---|---|
| 1 | HQ | 60 |
| 2 | QH | 75 |
| 3 | Q | 75 |

TABLE XII

| | Stability of Aerated Compositions (50° C.) | | | |
|---|---|---|---|---|
| Run No. | Air (ml) | MIT formulation (ml) | Air/MIT formulation (ml/mmole) | Stability Period (Days) |
| 1 | 290 | 10 | 29.6 | 50 |
| 2 | 270 | 30 | 9.4 | 45 |
| 3 | 200 | 100 | 2.0 | 12 |
| 4 | 50 | 250 | 0.2 | <6 |
| 5 | 6 | 294 | 0.02 | 4 |

What we claim is:

1. A method for stabilizing compositions comprising one or more 3-isothiazolinones, said method comprising adding to a composition comprising said one or more 3-isothiazolinones, an amount effective to stabilize said one or more 3-isothiazolinones of one or more stabilizing compounds having the formula:

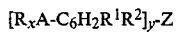

wherein Z is selected from the group consisting of $AR_x$, $R^1$, $R^2$, alkoxymethylene, methylene and alkylidene; R, $R^1$ and $R^2$ are independently selected from the group consisting of hydrogen, straight-chained, branched and cyclic alkyl, aryl and arylalkyl; A is oxygen or nitrogen, provided that when A is oxygen, x is 0 or 1 and when A is nitrogen, x is 1 or 2; and y is 1 or 2, so that degradation of said one or more 3-isothiazolinones is inhibited.

2. The method of claim 1, wherein at least one of said stabilizing compounds have the formula:

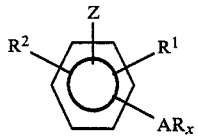

provided that when A is oxygen, x is 1 and when A is nitrogen, x is 2.

3. The method of claim 2, wherein at least one of said stabilizing compounds is selected from the group consisting of tert-butylcatechol, p-methoxyphenol, p-phenylenediamine, N,N'-di-sec-butyl-p-phenylenediamine, N,N'-diisopropyl-p-phenylenediamine, tert-butylhydroxyanisole, hydroquinone and quinhydrone.

4. The method of claim 1, wherein at least one of said stabilizing compounds has the formula:

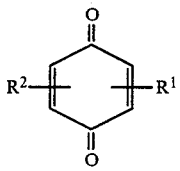

5. The method of claim 4, wherein at least one of said stabilizing compounds is selected from the group consisting of quinone and quinhydrone.

6. The method of claim 1, wherein said one or more 3-isothiazolinones are embedded in a solid support.

7. The method of claim 1, wherein said composition comprises an aqueous solution of said one or more 3-isothiazolinones.

8. The method of claim 1, wherein said composition comprises a solution of said one or more 3-isothiazolinones in an organic solvent having hydroxylic functional groups.

9. The method of claim 1, wherein said one or more stabilizing compounds are present in an amount less than about 10% by weight.

10. The method of claim 9, wherein said one or more stabilizing compounds are present in an amount between about 0.2 and about 5.0% by weight.

11. The method of claim 1, wherein said one or more 3-isothiazolinones comprise N-alkyl-isothiazolin-3-one and N-alkyl-5-chloro-isothiazolin-3-one.

12. The method of claim 11, wherein said one or more 3-isothiazolinones comprise N-methyl-isothiazolin-3-one and N-methyl-5-chloro-isothiazolin-3-one.

13. The method of claim 1, further comprising the step of adding to said one or more 3-isothiazolinones an amount of one or metal salts selected from the group consisting of metal nitrate stabilizers and salts of metals of Group IA and IIA of the Periodic Table of the elements, which amount is effective to synergistically improve said inhibition of said 3-isothiazolinones from degradation by said one or more stabilizing compounds.

14. The method of claim 13, wherein said one or more metal salts are selected from the group consisting of magnesium nitrate hexahydrate, $K_2HPO_4$, KH phthalate, magnesium acetate and potassium permanganate.

15. The method of claim 1, further comprising the step of aerating said 3-isothiazolinone composition after the step of adding said one or more stabilizing compounds.

16. In combination, a composition comprising one or more 3-isothiazolinones, and an amount effective to stabilize said one or more 3-isothiazolinones, of one or more stabilizing compounds having the formula:

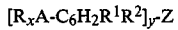

wherein Z is selected from the group consisting of $AR_x$, $R^1$, $R^2$, alkoxymethylene, methylene and alkylidine; R, $R^1$ and $R^2$ are independently selected from the group consisting of hydrogen, straight-chained, branched and cyclic alkyl, aryl and arylalkyl; A is oxygen or nitrogen, provided that when A is oxygen, x is 0 or 1 and when A is nitrogen, x is 1 or 2; and y is 1 or 2, so that degradation of said one or more 3-isothiazolinones is inhibited.

17. The combination of claim 16, wherein at least one of said stabilizing compounds have the formula:

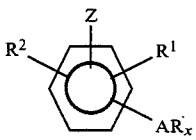

provided that when A is oxygen, x is 1 and when A is nitrogen, x is 2.

18. The combination of claim 17, wherein at least one of said stabilizing compounds is selected from the group consisting of tert-butylcatechol, p-methoxyphenol, p-phenylenediamine, N,N'-di-sec-butyl-p-phenylenediamine, N,N'-diisopropyl-p-phenylenediamine, tert-butylhydroxyanisole, hydroquinone and quinhydrone.

19. The combination of claim 16, wherein at least one of said stabilizing compounds has the formula:

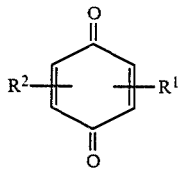

20. The combination of claim 19, wherein at least one of said stabilizing compounds is selected from the group consisting of quinone and quinhydrone.

21. The combination of claim 16, further comprising an amount of one or more metal salts selected from the group consisting of metal nitrate stabilizers and salts of metals of Group IA and IIA of the Periodic Table of the elements, which amount is effective to synergistically improve the stabilization of said 3-isothiazolinones by said one or more stabilizing compounds.

22. The combination of claim 21, wherein said one or more metal salts are selected from the group consisting of magnesium nitrate hexahydrate, $K_2HPO_4$, KH phthalate, magnesium acetate and potassium permanganate.

* * * * *

UNITED STATES PATENT AND TRADEMARK OFFICE
CERTIFICATE OF CORRECTION

PATENT NO. : 4,920,137
DATED : April 24, 1990
INVENTOR(S) : Segall et al.

It is certified that error appears in the above-identified patent and that said Letters Patent is hereby corrected as shown below:

Column 6, line 15, "±8%" should read --±0.8%--.

Signed and Sealed this

Twenty-eight Day of March, 1995

Attest:

BRUCE LEHMAN

Attesting Officer

Commissioner of Patents and Trademarks